US005621035A

United States Patent [19]
Lyles et al.

[11] Patent Number: 5,621,035
[45] Date of Patent: Apr. 15, 1997

[54] CERAMIC FUSED FIBER ENHANCED DENTAL MATERIALS

[75] Inventors: Mark B. Lyles; Ronald G. Ritsco, both of San Antonio, Tex.

[73] Assignee: M.E.D. USA, San Antonio, Tex.

[21] Appl. No.: 386,305

[22] Filed: Feb. 8, 1995

[51] Int. Cl.$^6$ .............................. C08K 3/38; C08K 3/08; C08K 3/40; A61F 2/00
[52] U.S. Cl. ........................ 524/404; 523/115; 523/116; 433/226; 433/228.1; 524/441; 524/492
[58] Field of Search ................................... 523/115, 116; 433/226, 228.1; 524/404, 441, 492

[56] References Cited

U.S. PATENT DOCUMENTS

| | | | |
|---|---|---|---|
| 3,721,644 | 3/1973 | Stoffey et al. | 260/41 A |
| 4,650,847 | 3/1987 | Omura et al. | 523/115 |
| 5,273,559 | 12/1993 | Hammar et al. | 51/298 |

OTHER PUBLICATIONS

Gee, et al. Jan. 1993 True linear polymerization shrinkage of unfilled resins and composites determined with a linometer; Dental materials, vol. 9, pp. 11–14.

Feilzer, et al. Jan. 1993 Setting stresses in composites for two different curing modes; Dental Materials, vol. 9, pp. 2–5.

Hosoda et al. Dec. 1990 SEM and elemental analysis of composite resins; The Journal of Prosthetic Dentistry, vol. 64 No. 6, pp. 669–676.

Marshall, et al. Oct. 1988 Restorative Dental Materials: Scanning electron Microscopy and Xray Microanalysis; Scanning Microscopy, vol. 2, No. 4, pp. 2007–2028.

Johnson, et al. Aug. 1971 Effects of various finishing devices on resin surfaces; JADA, vol. 83, pp. 321–331.

Jaarda, et al. Apr. 1993 Measurement of composite resin filler particles by using scanning electron microscopy and digital imaging; The Journal of Prosthetic Dentisity, vol. 69, No. 4, pp. 416–424.

Bowen, Antonucci May–Jun. Dimethacrylate Monomers of Aromatic Diethers; Journal of Dental Resins, pp. 599–604.

Kilfoil, et al. Jul. 1983 The tensile strength of a composite resin reinforced with carbon fibers; The Journal of Prosthetic Denstistry vol. 50, No. 1, pp. 40–43.

Hadavi, et al. Resin/Amalgam Bond Strength; Assessing Microleakage (Operative Dentistry).

Neo, et al. Dec. 1986 Effects of polymerization techniques of uniformity of cure of large–diameter, composite restorations; JADA, vol. 113, pp. 905–909.

Bowen Feb. 1967 Adhesive bonding of various materials to hard tooth tissues; JADA, vol. 74, pp. 439–445.

Asmussen Jan. 1975 NMR–analysis of monomers in restorative resins; Acta Odont. Scand. vol. 33, pp. 129–134.

Brauer, et al. 1979 Effect of Diluent on the Properties of Bis–GMA Based Composites; IADR Abstracts, p. 243.

Raptis, et al. 1979 Physical and Mechanical Properties of New Composite Resins; IADR Abstracts, p. 259.

Tani, Ida 1979 A Comparison of the Physical Properties of Four UV–Cured Composite Restorative Materials; IADR Abstracts, p. 262.

Antonucci, Bowen Feb. 1976 Dimethacrylates Derived From Hydroxybenzoic Acids; J. Dent. Res., vol. 55, No. 1, pp. 8–15.

Caldwell, et al. Oct. 1957 Microhardness studies of intact surface enamel; J. Dent. Res., vol. 36, No. 5, pp. 732–738.

Ryge et al. Dec. 1961 Micro–identation Hardness; J. Dent. Res., vol. 40, No. 6, pp. 1116–1126.

Atmadja 1990 Some factors influencing the depth of cure of visible light–activated composite resins; Australian Dental Journal, vol. 35, No. 3, pp. 213–218.

Braem, et al. May 1986 The Impact of Composite Structure on Its Elastic Response; J. Dent. Res., vol. 65, No. 5, pp. 648–653.

Nakayama, et al. Sep.–Oct. 1974 Elastic Properties of Dental Resin Restorative materials; J. Dent. Res., vol. 53, No. 5, pp. 1121–1126.

Fan, et al. Nov. 1979 In vitro Wear of Microfilled and Visible Light–cured Composites; J. Dent Res, vol. 58, No. 11, pp. 2116–2119.

Mitchem, Gronas Dec. 1985 The continued in vivo evaluation of the wear of restorative resins; JADA Research Reports, vol. 111, pp. 961–964.

Craig Apr. 1981 Chemistry, Composition, and Properties of Composite Resins; Dental Clinics of North America, vol. 25, No. 2, pp. 219–239.

Leinfelder Apr. 1981 Composite Resins in Posterior Teeth; Dental Clinics of North America, vol. 25, No. 2, pp. 357–364.

Willems, et al. Sep. 1991 The Surface Roughness of Enamel–to–Enamel Contact Areas Scared with the Intrinsic Roughness of Dental Resin Composites; J. Dent. Res., vol. 70, No. 9, pp. 1299–1305.

Fan, Powers Dec. 1980 In vitro Wear of Aged Composite Restorative Materials; J. Dent Res., vol. 59, No. 12, pp. 2066–2070.

Hosoda, et al. Dec. 1990 SEM and elemntal analysis of composite resins; Journal of Prosthetic Dentistry, vol. 64, No. 6, pp. 669–676.

Bowen, Marjenhoff Sep. 1992 Dental Composites/Glass Ionomer: The Materials; Adv. Dent. Res., vol. 6, pp. 44–49.

(List continued on next page.)

Primary Examiner—Paul R. Michl
Assistant Examiner—LaVonda R. Dewitt
Attorney, Agent, or Firm—Bardehle Pagenberg Dost Altenburg Frohwitter Geissler and Partners

[57] ABSTRACT

The preferred embodiment of the present invention provides novel and unique filler compositions and ceramic enhanced dental materials. The preferred embodiment of the filler composition and the ceramic dental restorative material is comprised of about 22% by weight alumina, about 78% by weight silica, about 2% by weight silicon carbide, and about 2.85% by weight boron nitride with less than 1% cristobalite contamination.

21 Claims, 7 Drawing Sheets

OTHER PUBLICATIONS

Willems, et al. Sep. 1992 A classification of dental composites according to their morphological and mechanical characteristics; Dental Materials, vol. 8, pp. 310–319.

Jun. 1977 New American Dental Association Specification No. 27 for Direct Filling Resins; Reports of Councils and Bureaus/JADA, vol. 94, pp. 1191–1194.

Leinfelder Apr. 1985 Composite Resins; Dental Clinics of North America, vol. 29, No. 2, pp. 359–371.

Lutz, Phillips Oct.1983 A classification and evaluation of composite resin systems; Fixed Prosthodontics/Operative Dentistry, vol. 50, No. 4, pp. 480–488.

Lambrechts, Vanherle 1983 Structural evidences of the microfilled composites; Journal of Biomedical Materials Research, vol. 17 pp. 249–260.

Craig May 1979 Selected Properties of Dental Composites; J. Dent. Res., vol. 58, No. 5, pp. 1544–1550.

Braem, et al. Sep. 1989 Mechanical properties and filler fraction of dental composite; Dental Materials, vol. 5, pp. 346–349.

Ameye, et al. Dec. 1981 Conventional and microfilled composite resins. Part I: Color stability and marginal adaptation; Journal of Prosthetic Dentistry, vol. 46, No. 6, pp. 623–630.

Lutz, Phillips Oct. 1983 A classification and evaluation of composite resin systems; Fixed Prosthodontics/Operative Dentistry, vol. 50, No. 4, pp. 480–488.

Robinson, McCabe Nov. 1993 Impact strength of acrylic resin denture base materials with surface defects; Dental Materials, vol. 9, pp. 355–360.

Bowen Jan. 1963 Properties of a silica–reinforced polymer for dental restorations; Journal of the American Dental Association, vol. 66, pp. 57–64.

Bowen Oct. 1964 Effect of particle shape and size distribution in a reinforced polymer; Journal of the American Dental Association, vol. 69, pp. 481–495.

Mabie, Menis 1978 Microporous Glassy Fillers for Dental Composites; Journal of Biomedical Materials Research, vol. 12, pp. 435–472.

Soderholm Nov. 1981 Degradation of Glass Filler in Experimental Composites; J. Dent. Res., vol. 60, No. 11, pp. 1867–1875.

Ruyter Aug. 1988 Composites–Characterization of Composite Filling Materials: Reactor Response; Adv. Dent. Res., vol. 2, No. 1, pp. 122–129.

Leinfelder Aug. 1988 Current Developments in Posterior Composite Resins; Adv. Dent. Res., vol. 2, No. 1, pp. 115–121.

Raptis, et al. Oct. 1979 Properties of microfilled and visible light–cured composite resins; JADA, vol. 99, pp. 631–633.

Lacy Mar. 1987 A critical look at posterior composite restorations; JADA, vol. 114, pp. 357–362.

Hinoura, et al. Feb. 1987 Tensile bond strength between glass ionomer cements and composite resins; JADA, vol. 114 pp. 167–172.

Dennison, Craig Jul. 1972 Physical properties and finished surface texture of composite restorative resins; JADA, vol. 85, pp. 101–108.

Asmussen 1985 Clinical Relevance of Physical Chemical, and Bonding Properties of Composite Resins; Operative Dentistry, vol. 10, pp. 61–73.

Davidson, et al. Feb. 1984 Relaxation of Polymerization Contraction Stresses by Flow in Dental Composites; J. Dent. Res., vol. 63, No. 2, pp. 146–148.

Stanford, et al. Nov. 1987 Radiopacity of light–cured posterior composite resins; JADA, vol. 115, pp. 722–724.

Fan, et al. Jan. 1985 Alternative Interpretations of Water Sorption Values of Composite Resins; J. Dent. Res. vol. 64, No. 1, pp. 78–80.

Dennison, et al. Apr. 1978 Color of Dental Restorative Resins; J. Dent. Res., vol. 57, No. 4, pp. 557–562.

Ferracane, et al. Sep. 1981 Rheology of Composite Restoratives; J. Dent. Res., vol. 60, No. 9, pp. 1678–1685.

Hirasawa, et al. Jan. 1983 Initial Dimensional Change of Composite in Dry and Wet Conditions; J. Dent. Res., vol. 62, No. 1, pp. 28–31.

Oysaed, Ruyter Nov. 1986 Water Sorption and Filler Characteristics of Composites for Use in Posterior Teeth; J. Dent. Res., vol. 65, No. 11, pp. 1315–1318.

Powers, et al. Feb. 1979 Thermal Expansion of Composite Resins and Sealants; J. Dent. Res., vol. 58 No. 2, pp. 584–587.

Braden Aug. 1988 Some Aspects of the Chemistry and Physics of Dental Resins; Adv. Dent. Res., vol. 2, No. 1, pp. 93–97.

Valittu A Review of Reinforcing the Polymethyl Methacrylate with Metal Strengtheners; pp. 1–40 plus figures.

Goldberg, Burstone May 1992 The use of continuous fiber reinforcement in dentistry; Dental Materials, vol. 8, pp. 197–202.

Ritsco Sprg. 1994 Applications of Fibers in Prosthetic Dentistry; Dental Material and Research, pp. 1–13.

Ehrnford Oct. 1981 Composite Resins with a Condensable Inorganic Phase; J. Dent. Res., vol. 60, No. 10, pp. 1759–1766.

Ehrnford 1976 A method for reinforcing dental composite restorative materials; Odont. Revy, vol. 27, pp. 51–54.

Cross, et al. Jul. 1983 The Relationship Between Filler Loading and Particle Size Distribution in Composite Resin Technology; J. Dent. Res., vol. 62 No. 7, pp. 850–852.

Ehrnford 1984 Surface characteristics of composite resins comprising a porous reinforcing filler, an in vivo study; Acta Odontol Scand, vol. 42 pp. 59–64.

Latour, Black 1992 Development of FRP composite structural biomaterials: Ultimate strength of the fiber/matrix interfacial bond in vivo simulated environments; Journal of Biomedical Materials Research, vol. 26, pp. 593–606.

Kilfoil, et al. Jul. 1983 The tensile strength of a composite resin reinforced with carbon fibers; Journal of Prosthetic Dentistry, vol. 50, No. 1, pp.40–43.

Krause, et al. 1989 Mechanical properties of BIS–GMA resin short glass fiber composites; Journal of Biomedical Materials Research, vol. 23, pp. 1195–1211.

Goldberg, et al. 1994 Screening of matrices and fibers for reinforced thermoplastics intended for dental applications; Journal of Biomedical Materials Research, vol. 28, pp.167–173.

Bowman, Manley 1984 The Elimination of Breakages in Upper Dentures by Reinforcement with Carbon Fibre; British Dental Journal, vol. 156, pp. 87–89.

Smith Nov. 1962 Recent Developments and prospects in dental polymers; British Dental Journal, vol. 12, No. 6, pp. 1066–1078.

Grant, Greenert Feb. 1967 Whisker reinforcement of polymethyl methacrylate denture base resins; Australian Dental Journal, pp. 29–33.

DeBoer, et al. 1984 The effect of carbon fiber orientation on the fatigue resistance and bending properties of two denture resins; Journal of Prosthetic Dentistry, pp. 119–121.

Schreiber Jul. 1974 The clinical application of carbon fibre/polymer denture bases; British Dental Journal, vol. 137, p. 21.

Valittu, 1992 Reinforcement of acrylic resin denture base material with metal or fiber strenghteners; Journal of Oral Rehabilitation, vol. 19, pp. 225–230.

Grave, et al. 1985 Denture base acrylic reinforced with high modulus fibre; Dental Materials, vol. 1, pp. 186–187.

Skirvin et al. Dec. 1982 Polymethylmethacrylate Reinforcement: Effect on Fatigue Failure; Military Medicine, vol. 147, pp.1037–1040.

Grave et al. 1985 Denture base acrylic reinforced with high modulus fibre; Dental Materials, vol. 54, No. 1, pp.185–187.

Ruffino Jul. 1985 Effect of steel strengtheners on fracture resistance of the acrylic resin complete denture base; Journal of Prosthetic Dentistry, vol. 54, No. 1, pp. 75–78.

Schreiber Jan. 1971 Polymethylmethacrylate Reinforced with Carbon Fibres; British Dental Journal, vol. 130, pp. 29–30.

Gutteridge 1992 Reinforcement of poly (methylmethacrylate) with ultra–high–modulus polyethylene fibre; J. Dent. Res., vol. 20, pp. 50–54.

Braden et al. 1988 Denture base poly(methyl methacrylate) reinforced with ultra–high modulus polyethylene fibres, British Dental Journal, vol. 164, pp. 109–112.

Andreopoulos, et al. Jan. 1991 Surface treated polyethylene fibres as reinforcement for acrylic resins; Biomaterials, vol. 12, pp. 83–87.

Gutteridge 1988 The effect of including ultra–high–modulus polyethylene fibre on the impact strength of acrylic resin; British Dental Journal vol. 164, pp.177–180.

Salem Abdul–Latif Salem Some Properties of Reinforced Denture Base Polymers; No. 345.

Ekstrand, Ruyter Jan. 1986 Implant–fixed, dental bridges from carbon/graphite fibre reinforced poly (methyl methacrylate); Biomaterials, vol. 7, pp. 73–75.

O'Brien 1989 Dental Materials; Properties and Selection; Quintessence Publishing Co., Inc. pp. 157–170.

Ruyter, et al. 1986 Development of carbon/graphite reinforced poly(methyl methacrylate) suitable for implant–fixed dental bridges; Dental Materials, vol. 2, pp. 6–9.

Malquarti, et al. Mar. 1990 Prosthetic use of carbon fiber––reinforced epoxy resin for esthetic crowns and fixed partial dentures; Journal of Prosthetic Dentistry, vol. 63, No. 3, pp. 251–257.

Markus 1994 An indirect/direct combined approach for a reinforced bridge; Journal of the New Jersey Dental Association/Winter 1994, pp. 23–26.

Nov. 1993 "GlasSpan Flexible Ceramic Bonded Reinforcement Material–The Indirect GlasSpan Bridge; Product Spotlight, Trends & Techniques"; pp. 24–25.

Altieri, et al. Jan. 1994 Longitudinal clinical evaluation of fiber–reinforced composite fixed partial dentures: A pilot study; Journal of Prosthet Dentistry, vol. 71, No. 1, pp. 16–22.

Burgess, et al. mar. 1994 Flexural Strength of Five Provisional Materials; IADR General Session and Exhibition, Seattle WA.

Andrepoulous, et al. 1992 Reinforcement of acrylic polymers with rediopaque cellulose fibres; Journal of Material Science; vol. 27, pp. 734–736.

Willems, et al. 1993 Composite resins in the 21st century; Quintessence International vol. 24, No. 9, pp. 641–657.

Albers, et al. 1991 ADEPT Report; vol. 2, No. 4, pp. 53–64.

Farah, et al. 1991 Anterior and Posterior Composites; The Dental Advisor, vol. 8, No. 4, pp. 1–8.

Figure 8

| Product | P.R.I.M.M.™ | Restolux SP-4™ | Z100 (3M) | XRV Herco. | TPH Prisma | Heliomolar | Charisma |
|---|---|---|---|---|---|---|---|
| Filler | Alumina/Silica (Fused Glass Fibers) | Glass Ceramic Fibers | Zirconia/ Silica | Barium Glass | Barium Glass | $SiO_3$ | Barium Glass/ Microglass |
| Filler loading Wt (%) | 60 | 68.5 | 66 | 56 | 53 | 38 | 73 |
| Average Particle Size (microns) | 180/0.4 | 300 | 0.6 | 0.6 | 1 | Microfil** | 0.7 |
| Diametral Tensile (MPa) | 82 | ** | 83 | 81 | 72 | 47 | 77 |
| Compressive Strength (MPa) | 560 | ** | 448 | 324 | 375 | 436 | 399 |
| Hardness (Kg/mm2) | 50 | 125 | 78.3 | 53.3 | 43.5 | 35.9 | ** |
| Y-Modulus (Pa) | $25 \times 10^9$ | $23 \times 10^9$ | $13 \times 10^9$ | $7.6 \times 10^9$ | $5.7 \times 10^9$ | $4.3 \times 10^9$ | ** |
| Surface Roughness (Ra) | 0.30 | 1.19 | 0.27 | 0.12 | 0.29 | .013 | ** |
| Coeff of Thermal Expansion x $10^6$ unit/unit/C | 10 | 17 | 17 | 27 | 30 | 52 | 38 |
| Radiopacity | TPB***[Yes] | Yes | Yes | Yes | Yes | Yes | Yes |

** Data unavailable.

CERAMIC FUSED FIBER ENHANCED DENTAL MATERIALS

FIELD OF THE INVENTION

This invention relates to dental restorative materials. In another respect, the invention relates to ceramics and ceramic composite restorative materials. Yet in another aspect, the invention relates to novel restorative compositions, including but not limited to, silver-based mercury amalgams and plastic-based denture materials for the direct restoration or replacement of teeth. In a further aspect, the invention relates to novel restorative compositions for the direct filling of posterior teeth.

BACKGROUND OF THE INVENTION

Dental restorative materials include materials used to repair damaged teeth and/or replace missing teeth and/or other related oral structures. In some instances, dental restorative materials include materials used to reconstruct the maxillofacial complex. In general, dental restorative compositions include: (1) fillers, (2) binders, (3) dental amalgam, (4) enamel and dentin bonding agents, (5) dental composites, (6) dental cements, (7) casting alloys for crowns and bridges, (8) ceramic/metal materials, (9) denture and prosthetic materials, (10) porcelains, and (11) ceramic restorative materials, etc..

A variety of compositions have been proposed and used for the direct filling of teeth. Of these compositions, some may be generally classified as dental composites and more specifically as resin composites. These resin composites are comprised of inorganic particulates, i.e., filler, bound together with a polymeric matrix, i.e., a binder. The particulate filler reinforces the polymeric matrix and offsets its deficiencies. The binder, and/or polymeric matrix, may be comprised of an acrylic or epoxy resin or other types of carbon-based polymers. See, for example, U.S. Pat. Nos. 3,066,112 and 3,179,623 which are hereby incorporated by reference. Fillers for such composite compositions, both posterior and/or anterior dental use, include finely divided solids like silica, glass, zirconium, aluminum oxide, crystalline quartz, glass beads, or a mixture of glass beads and quartz. A material acceptable, however, for posterior use must be able to achieve a high filler loading capacity in the resin system. Moreover, filler strength, content, shape and size directly determines the physical and mechanical properties of the restoration material.

To date, there has been no composite material developed that completely meets the expected parameters needed for the intended use as a posterior dental restorative material to replace mercury-based dental amalgams. Dental materials presently available lack several physical or mechanical properties necessary for an ideal posterior dental restoration. As noted, it is imperative to achieve a high filler loading capacity in the resin system and presently all attempts to achieve such have failed. For example, highly loaded materials such as Microfine Composite™, using colloidal silica of a 40 nm size result in dramatically increased viscosity which jeopardizes handling characteristics. (See, Lambrechts, P; Vanherle, G. (I1983); *Structural Evidence of Microfilled Composites. J. Biomed Mater Res* 17: 249–60.; Willems, G; Lambrechts, P.; Braen, M.; Celis, J. P.; Vanherle, G. (1993): *A Classification of Dental Composites according to their Morphology and Mechanical Characteristics. Dent Mater* 8: 310–19). The colloidal silica forms an extended network structure that produces an increase in viscosity thereby limiting the amount of filler that can be incorporated to around 50% by volume. This 50% volume of filler loading has only been obtained by first filling to higher degree, that is, greater than 50% during manufacturing, and then curing under high temperature and grinding to make colloidal oxide field resin particles (organic fillers). However, a major problem still remains. The interface between these particles and the matrix, i.e., binder, is weak and causes brittle failure and wear. The filler composition of the present invention has the characteristics needed for posterior composite materials when combined with a resin matrix to address and solve these major hurtles.

The properties needed for an advantageous dental restorative material include, inter alia, the following: (1) low to high density, (2) high tensile/compression strength (3) low thermal conductivity, (4) purity, (5) long life in cyclic applications, (6) high flexural strength, (7) rigidity, (8) inertness, (9) dimensional stability, (10) thermal shock resistance, (11) high diffusitivity, and (12) porosity. The present invention provides heretofore unknown fused-fibrous dental restorative materials with the above properties.

SUMMARY OF THE INVENTION

An object of the present invention is to provide fused-fibrous filler compositions useful in dental fillings and materials that are particularly useful in dental restorative compositions, prosthedontic applications, and ceramic restorative materials, which have improved handling characteristics, improved strength, improved wear resistance, and decreased shrinkage from polymerization as compared to presently available dental restorative compositions, dental prosthetic devices, and ceramic restorative materials. The composition of the present invention also contains less than 1% cristobalite contamiation. It has been discovered that significantly improved particulates that are useful as fillers in dental restorative and prosthetic compositions are obtained from fused-fibrous compounds of the following composition: (1) from about 1% to about 50% by weight alumina; (2) from about 50% to about 98% by weight silica; and (3) from about 1% to about 5% by weight boron nitride. In addition, the composition may further comprise silicon carbide up to about 3% by weight.

BRIEF DESCRIPTION OF THE DRAWINGS

FIG. 8 is a table which provides a comparison of the properties of the filler component of the present invention as compared to prior art filler components.

DESCRIPTION OF THE PREFERRED EMBODIMENTS

Figure 1A:
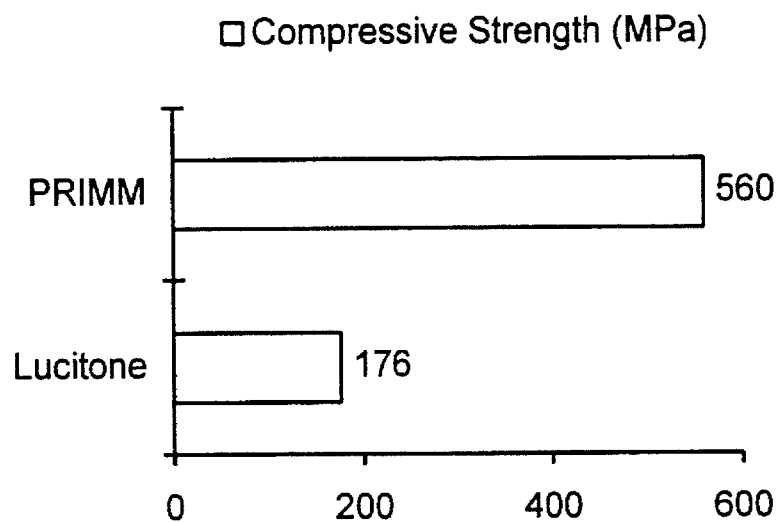
FIGS. 1*a* and 1*b* are tables of the parameters of P.R.I.M.M.™ vs. Lucitone 199 Denture Acrylic.
Figure 1B:
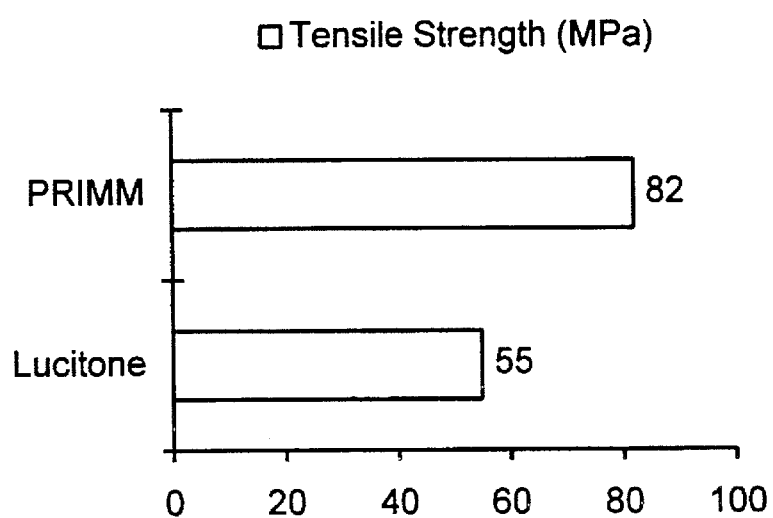
Figure 2A:
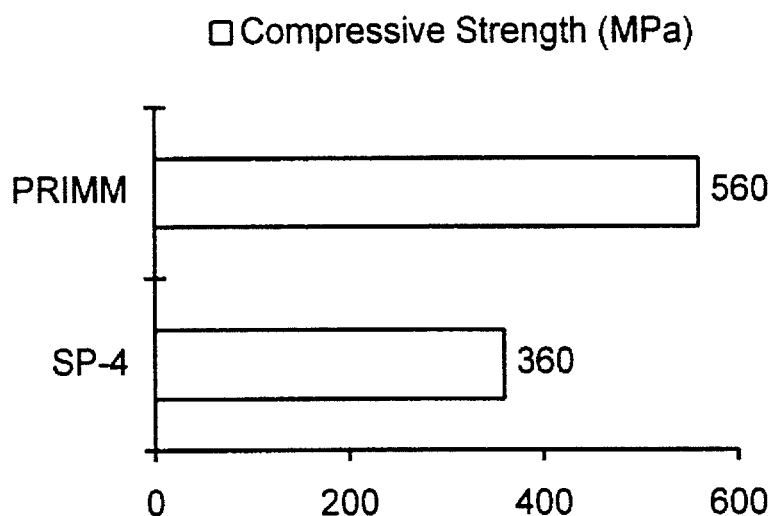
FIGS. 2*a* and 2*b* are tables of the parameters of P.R.I.M.M.™ vs. Restolux SP-4 Composite Resin (Chopped Fibers).
Figure 2B:
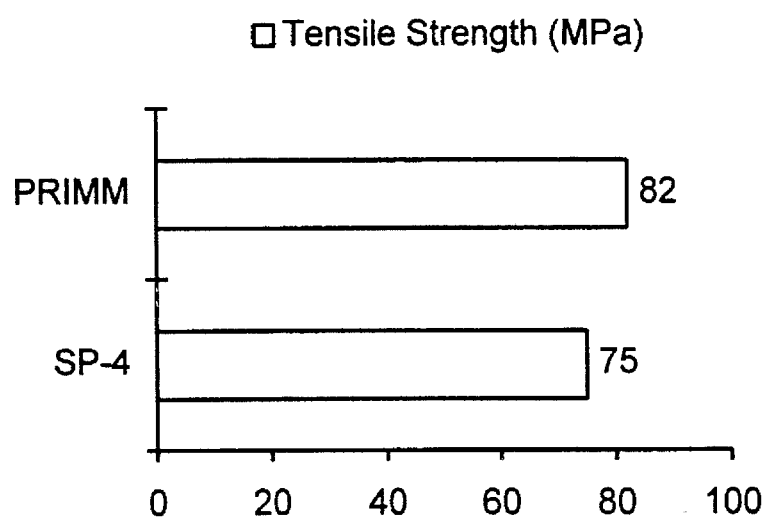
Figure 3A:
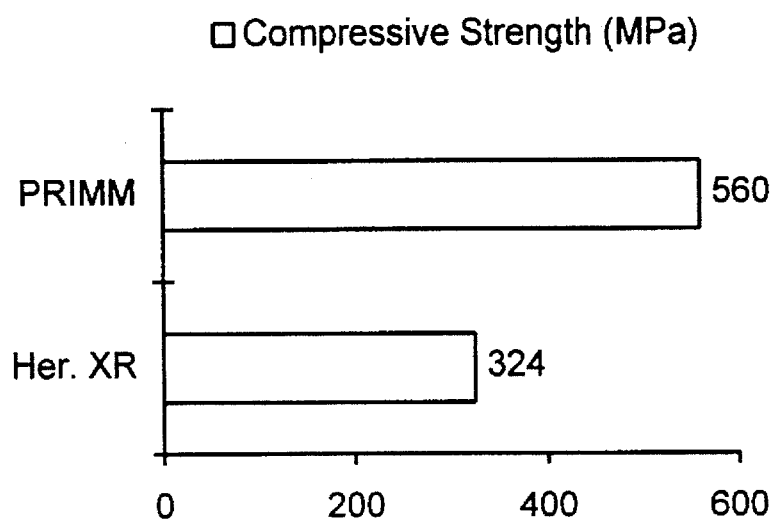
FIGS. 3*a* and 3*b* are tables of the parameters of P.R.I.M.M.™ vs. Herculite XRV (Kerr) Composite Resin.
Figure 3B:
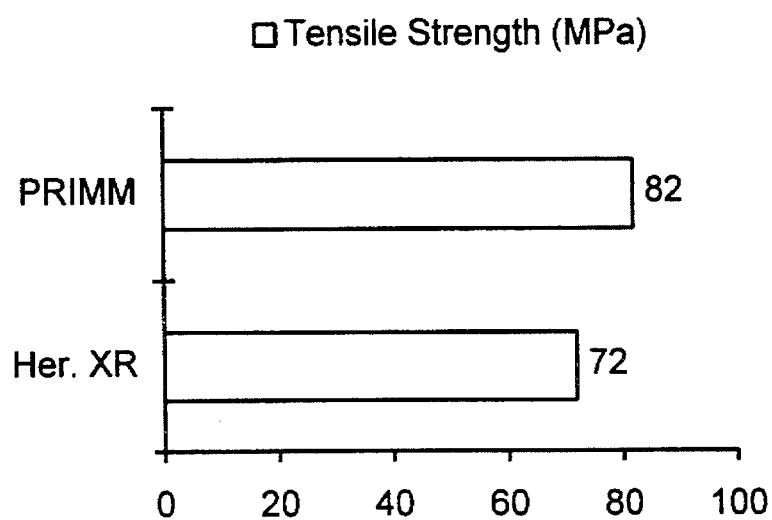
Figure 4A:
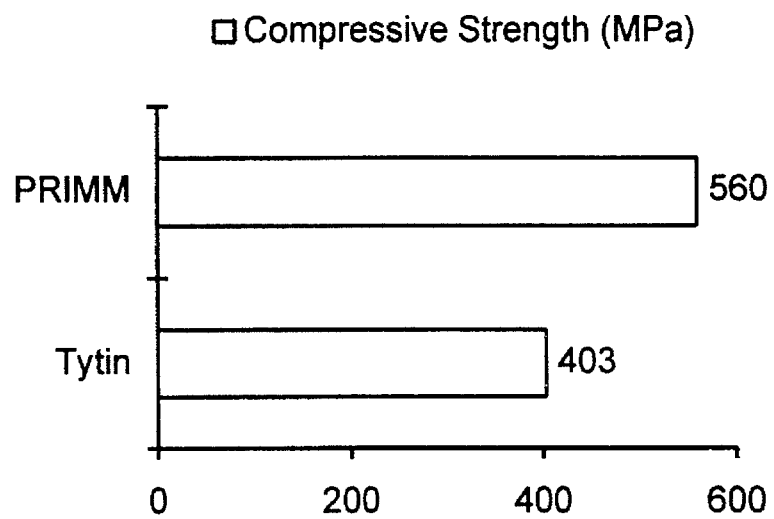
FIGS. 4*a* and 4*b* are tables of the parameters of P.R.I.M.M.™ vs. Tytin Amalgam Alloy.
Figure 4B:
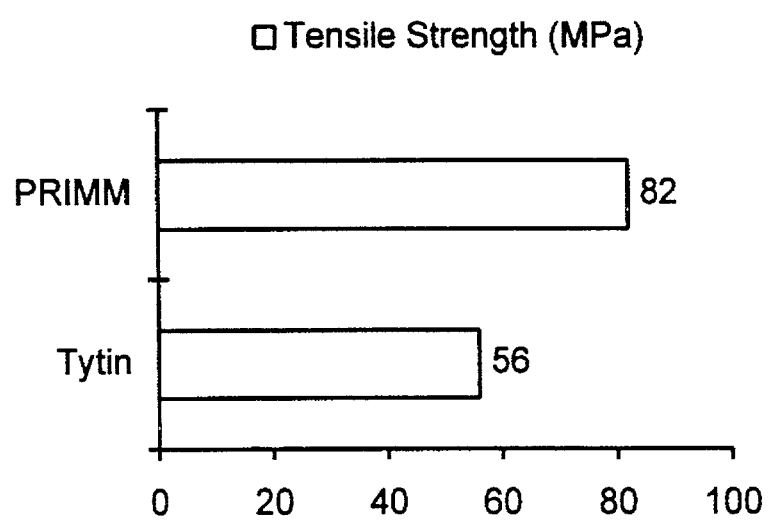

Generally, the filler component of the present invention has been described above in the Summary Of The Invention. However, several fused-fibrous flier compositions falling within the description set forth above are particularly preferred. Generally, the compositions of the present invention can be comprised of alumina fibers, silica fibers, and from about 1% to about 5% boron, preferably boron nitride.

One preferred embodiment is comprised of a binder and a filler wherein said filler is comprised of about 1% to about 50% by weight alumina, from about 50% by weight to about 98% by weight silica, and boron. Another preferred embodiment is comprised of: (1) from about 15% to about 30% by weight alumina fiber; (2) from about 65% to about 85% by weight silica fiber; (3) from about 1% to about 3% by weight silicon carbide; and (4) from about 1% to about 5% by weight boron nitride.

Another more preferred fused-fibrous composition for the filler is as follows: (1) about 21% by weight alumina fiber; (2) about 74% by weight silica fiber; (3) about 2% by weight silicon carbide; and (4) about 2.85% by weight boron nitride. Preferably, the material of the present invention is comprised of alumina and silica fibers in a ratio of 22:78.

The ceramic restorative materials of the present invention have the advantageous properties outlined above needed for dental restorative composites and prosthetic materials. The filler material alone, has exceptional physical, chemical, and mechanical properties including, inter alia: (1) low to high density—4 lb./ft.$^3$ to 62 lb./ft.$^3$; (2) low thermal conductivity—e.g., for 12 lb./ft.$^3$ density at 500° F. conductivity=0.61 Btu-in./ft.$^2$; (3) purity-predominately comprised of 99.7% pure silica fibers and 95.2% pure alumina fibers; (4) long life in cyclic applications—e.g., 12 lb./ft.$^3$ density, does not degrade with cyclic exposure to 2600° F. and can even withstand limited exposure to 2900° F.; (5) rigidity-maintains shape and supports mechanical loads while providing thermal insulation (i.e., has a high compressive strength and tensile strength (MN/m2) (6) high flexural strength—modulus of rupture for 4 lb./ft.$^3$ to 62 lb./ft.$^3$ densities ranges from 100–6200 lb./in.$^2$; (7) inert—does not burn, softens at temperatures above 2700° F. and melts at about 3100° F.; (8) dimensional stability—has a low coefficient of thermal expansion and 0.4% linear shrinkage; (9) thermal shock resistance—can be heated to 2600° F. and immediately immersed in cold water without damage; (10) high diffusivity—12 lb:/ft.$^3$ to 62 lb./ft.$^3$ ranges from 97% to 56%; (11) porosity—highly porous and offers minimal resistance to the passage of gases or liquids; (12) able to coat or bond to other materials (i.e., materials, plastics, inorganics) with relative ease to enhance characteristics. In addition, the 16 lb./ft.$^3$ density filler material of the present invention has (1) a flexaral modulus of strength—2.5=10$^{10}$ Pa, (2) a Rockwell Hardness—50, (3) Surface Roughness of 0.6 Ra, and (4) linear shrinkage of 0.4% after repeated cycles at temperatures above 2700° F. As a result, the composite made with the flier of the present invention has a heretofore unknown linear shrinkage of 0.09%.

Generally, the process for the manufacture of fused-fibrous silica/alumina and/or other ceramic fiber of low density, like 12 lb. per ft.$^3$, is comprised of the following steps:

(1) preparation of a slurry mixture comprised of premeasured amounts of purified fibers and deionized water;

(2) removal of shot from slurry mixture;

(3) removal of water after thorough mixing to form a soft billet;

(4) addition of a ceramic binder after the formation of the billet;

(5) placement of the billet in a drying microwave oven for moisture removal; and (6) sintering the dry billet in a large furnace at about 1600° F. or above.

The high purity silica fibers above are first washed and dispersed in hydrochloric acid and/or deionized water or other solvents. The ratio of washing solution to fiber is between 30 to 150 parts liquid (pH 3 to 4) to 1 part fiber. Washing for 2 to 4 hours generally removes the surface chemical contamination and non-fibrous material (shot) which contributes to silica fiber devitrification. After washing, the fibers are rinsed 3 times at approximately the same liquid to fiber ratio for 10 to 15 minutes with deionized water. The pH is then about 6. Excess water is drained off leaving a ratio of 5 to 10 pans water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 pans water with 1 pan fiber in a V-blender for 2½ to 5 minutes. The time required is a function of the fiber length and diameter. In general, the larger the fiber, the more time required.

Generally, in order to manufacture ultra low density fused-fibrous ceramic filler material, for example, densities below 12 lb/ft$^3$, the process includes the additional steps of:

(1) the addition of expandable carbon fibers in the casting process and/or other temporary support material; and (2) firing the billet at about 1300° F. to remove the carbon fibers or other support material prior to the final firing at approximately 1600° F. or above.

When the dispersed silica fibers and dispersed alumina fibers are combined, the pH is probably acidic and should be adjusted to neutral with ammonium hydroxide. The slurry should contain about 12 to about 25 pans water to about 1 part fiber. The slurry is mixed to a uniform consistency in a V-blender in 5 to 20 minutes. The boron nitride can be added at this point (2.85% by weight of the fibers) and mixed to a uniform consistency in a V-blender for an additional 5 to 15 minutes creating a Master Slurry. The preferred mixing procedure uses 15 parts water to 1 part fiber and the slurry is produced in about 20 minutes of mixing. At lower density formulations, expendable carbon fibers are used to give "green" strength to the billet prior to the final sintering. The percent of carbon fiber used varies greatly depending on the diameter, length and source of the fiber and the ultimate density of the material being produced. The percent of carbon fiber per dry weight of material should range between 1 and 10%. The source of the carbon fiber can take many forms including nylon, cellulose, and purified graphite based carbon in fibrous form. Carbon fibers added in the casting process are eliminated by firing the billets at 1350° F. prior to the final firing at 2450° F.

The Master Slurry is poured into a mold for pressing into the desired shape. The water is withdrawn rapidly and the resulting felt is compressed at 10 to 20 psi. Rapid removal of the water is required to prevent the fibers from separating. If graded properties are desired in the resultant material, the slurry can be allowed to settle and the fibers to partially separate before the removal of the water.

The final density of the finished restorative material is determined in part by the mount of compression placed on the felt, varying the wet molded dimension in relation to the fiber content. The formulation of the present invention has been prepared in densities ranging from about 0.05 to 0.48 g/cc. It can, however, be prepared in lower and higher densities.

After molding, the restorative material is dried and fired by the following preferred procedure. The material is first dried in an oven for 18 hours; the temperature, initially 380° C., is raised at a rate of 11° C. per hour to 104° C., held there for 4 hours, raised again at a rate of 11° C. per hour to 150° C., and held there for 4 hours. The material is taken directly from the drying oven, placed in the firing furnace, and fired. A temperature rise rate of 2200° C. per hour or less is required in order to avoid cracking and warping in the case of a 15 cm×15 cm×7.5 cm block of material. For larger blocks, slower heating rates may be required. The maximum firing temperature may vary from 1200° C. to 1600° C. depending upon the fiber ratio used, mount of boron nitride, and the final density of the material that is desired.

The temperature rise rate is chosen to permit relatively uniform temperatures to be achieved throughout the material during the process. A faster temperature rise rate causes non-uniform temperatures to be achieved throughout the material during the process. A faster temperature rise rate causes nonuniform strength and density and may cause cracking. Longer or higher temperature firing results in higher shrinkage and related greater resistance to subsequent shrinkage, as well as a shorter lifetime to devitrification. The maximum firing temperature is dependent upon the fiber ratio used and the density of the composite desired. The firing time and maximum temperature are selected to allow sufficient shrinkage to achieve stabilization while not allowing any devitrification.

After firing, the material may be machined to obtain any desired final dimensions. Only about 0.5 cm of the material must be machined off.

The procedure used to prepare this restorative material, i.e., the polymeric rigid inorganic matrix material of the present invention, may be varied through a rather broad range with satisfactory results. In one variation, the silica fibers may be borated and prefired prior to use. This process is used to improve the morphological stability and physical properties of the resultant material.

The following examples are provided to illustrate the invention by describing various embodiments, including its best mode as presently conceived. All proportions used are expressed on a percent by weight basis unless otherwise noted.

EXAMPLE 1

An embodiment of the fused-fibrous matrix ceramic material of the present invention having a density of 0.32 g/cc, and opacified with silicon carbide was produced, with 825 grams of silica fibers, 175 grams alumina fiber (average diameter–11 microns, length–0.32 cm), 35 grams 1200 grit silicon carbide, 28.5 grams of boron nitride, 10 milliliters hydrochloric acid, 5 milliliters ammonium hydroxide and deionized water. The silica fibers were washed as in Example 2.

The alumina fibers were placed in a 7,570 ml capacity stainless steel double shell blender with 5,000 grams deionized water and mixed using an intensifier bar for 2½ minutes to disperse the fiber.

The washed silica fibers, dispersed alumina fibers, boron nitride, and silicon carbide were placed in a 28.31 liter stainless steel double shell V-blender. Deionized water was added to bring the total weight to 15,000 grams. The ammonium hydroxide (5 ml) was added to adjust the slurry to basic before mixing. The slurry was mixed, degassed, transferred to a mold and pressed into a billet as in Example 2.

EXAMPLE 2

The materials used were the following: 150 grams aluminasilicate fibers (AS32, manufactured by 3-M Company containing 80% $Al_2O_3$ and 20% $SiO_2$), 1000 grams of silica fibers (Microquartz 108), 35 grams of 1200 grit silicon carbide, 30 grams of boron nitride, 10 ml of hydrochloric acid, 5 ml of ammonium hydroxide, and deionized water.

The silica fibers were placed in a polyethylene container in 32 liters of deionized water. Hydrochloric acid (10 ml) was added to bring the pH to 3. Pure nitrogen was bubbled through the mixture to agitate the fiber and assist washing. Agitation was continued for two hours. The acidic water was then drained off, fresh deionized water added and the mixture again agitated with pure nitrogen for 15 minutes. The timing process was repeated 2 more times which brought the pH to about 6.0.

The aluminasilicate fibers were placed in a 7,570 ml capacity stainless steel double shell blender with 5,000 grams of deionized water and mixed using the intensifier bar for 2½ minutes to disperse the fiber.

The washed silica fibers, dispersed aluminasilicate fibers, boron nitride, and silicon carbide were placed in a 28.31 liter stainless steel double shell V-blender. Deionized water was added to bring the total weight to 18,000 grams. Ammonium hydroxide (5 ml) was added to adjust the slurry to basic before mixing. The slurry was then mixed with the intensifier bar running for 20 minutes, removed from the V-blender and degassed, transferred into a mold, and pressed into a 21.6 cm×21.6 cm×10 cm billet. The top and bottom of the mold were perforated and covered with a 16 mesh aluminum screen to allow the excess water to flow out.

The billet was dried in an oven for 18 hours beginning at 38° C., increased at 11° C. per hour to 104° C., held for four hours at 104° C., increased at 11° C. per hour to 150° C. and held four hours at 150° C. After drying, the billet was transferred to the firing furnace. The furnace temperature was increased at a rate of 220° C. per hour to the firing temperature, 1315° C., where it was held for 1½ hours. After firing, the temperature was decreased at a rate of 220° C. per hour to 980° C. where the furnace was turned off, then allowed to cool to room temperature.

EXAMPLE 3

The usefulness of boron oxide in the two-fiber composites of this invention is demonstrated by the following preparations.

In one run, an experimental mixture was made containing 25% aluminasilicate fibers ("FIBERFRAX H," manufactured by the Carborundum Company, containing 62% $Al_2O_3$ and 38% $SiO_2$) and 75% pure silica fibers ("MICROQUARTZ 108"). The mixture was ground with mortar and pestle and then fired at 1400° C. for 5 hours. The resulting product underwent 48% devitrification. When the aluminasilicate fibers were prefired with boron oxide (85% and 15% respectively) at 1100° C. for 90 minutes and then mixed with the silica fibers and fired as above, the product exhibited no devitrivication.

EXAMPLE 4

An acceptable 17 cm×17 cm×7.5 cm billet of material having a density of 0.11 g/cc was produced using 600 grams of silica fibers, 90 grams of aluminaborosilicate fibers (average diameter–11 microns, 0.64 cm long), 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 3000 grams of deionized water for 5 minutes. The washed silica fibers, dispersed aluminaborosilicate fibers, and ammonium hydroxide were mixed, with enough deionized water to bring the total weight to 9,000 grams, in a 28.31 liter V-blender for 10 minutes with the intensifier bar running. The slurry was removed from the V-blender, degassed, molded and the resulting billet fired as in Example 2. The billet was then transferred to the firing furnace. The furnace temperature was increased at a rate of 220° C. per hour to the firing temperature, 1260° C., where it was held for 5 hours. After firing, the temperature was decreased at a rate of 220° C. per hour to 980° C., at which point the furnace was named off and allowed to cool to room temperature. The billet was machined to 17 cm×17 cm×7.5 cm in accordance with usual machining practices.

EXAMPLE 5

An acceptable 17 cm×17 cm×7.5 cm billet of material with yet greater stability toward devitrification than the material produced in Example 1, having a density of 0.32 g/cc, and opacified with silicon carbide was produced using 825 grams of silica fibers, 175 gram aluminaborosilicate fibers (average diameter—11 microns, 0.64 cm long), 35 gram of 1200 grit silicon carbide, 10 ml of hydrochloric acid, 5 ml of ammonium hydroxide, 56.8 grams of boron oxide, and deionized water.

The silica fibers were washed in accordance with the procedure of Example 2. The boron oxide was dissolved in 4,000 grams of deionized water (concentration—1.42% boron oxide). The aluminaborosilicate fibers were placed in a stainless steel basket and dipped into the boron oxide solution (the aluminaborosilicate fibers absorbed 7 times their own weight of the boron oxide solution). The fibers with absorbed boron oxide were then dried at 104° C. for 4 hours and calcined at 1100° C. for 1 hour. The "borated" fibers were then placed in a 7,570 ml capacity stainless steel V-blender with 5,000 grams of deionized water and mixed using the intensifier bar for 2 ½ minutes to disperse the fiber. The washed silica fibers, dispersed "borated" aluminaborosilicate fibers, silicon carbide, and ammonium hydroxide were mixed with enough deionized water to bring the total weight to 15,000 grams, in a one cubic foot V-blender for 20 minutes with the intensifier bar running. The slurry was removed from the V-blender, degassed, molded, dried, fired, and machined, as in Example 1.

EXAMPLE 6

An acceptable 17 cm×17 cm×7.5 cm billet of material with graded properties, having a density of 0.32 g/cc, and opacified with silicon carbide, was produced using 825 grams of silica fibers, 175 grams of aluminaborosilicate fibers (average diameter . 11 microns, 0.64 cm long), 35 grams of 1200 grit silicon carbide, 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 5000 grams of deionized water for 5 minutes. The washed silica fibers, dispersed aluminaborosilicate fibers, silicon carbide and ammonium hydroxide were mixed with enough deionized water to bring the total weight to 25,000 grams, in a 28.31 liter V-blender for 15 minutes with the intensifier bar running. The slurry was removed from the V-blender, degassed, molded, dried, fired and machined in accordance with the procedure of Example 1.

The resulting billet of material is relatively richer in silica at the top and aluminaborosilicate at the bottom.

EXAMPLE 7

A 17.5 cm×17.5 cm×9 cm material with a temperature capability greater than that of the material of Example 1, having a density of 0.24 g/cc, and opacified with silicon carbide, was produced using 750 grams of aluminaborosilicate fibers (diameter–1 to 3 microns), 250 grams of silica fibers, 35 grams of silicon carbide, 5 ml of ammonium hydroxide, and deionized water. The silica fibers were dispersed in a 7,570 ml V-blender with 5,000 grams of deionized water for 5 minutes.

The dispersed silica fibers, aluminaborosilicate fibers, silicon carbide, and ammonium hydroxide were mixed with enough deionized water to bring the total weight to 18,000 grams, in a 28.31 liters V-blender for 7 minutes with the intensifier bar running. The slurry was removed from the V-blender, degassed, molded, and dried as in Example 2. In the furnace, the temperature was increased at a rate of 220° C. per hour to the firing temperature, 1370° C. where it was held for 1½ hours. After firing, the temperature was decreased at a rate of 220° C. per hour to 980° C., at which point the furnace was turned off and allowed to cool to room temperature. The billet was machined to 17.5 cm×17.5×9 cm in accordance with the usual machining practices.

The preferred alumina fibers are 95.2% pure and are available from ICI Americas, Inc. and marketed as Saffril™. The preferred diameter for the alumina fibers ranges from 1 to about 15 microns. The preferred silica fibers are 99.7% pure and are available from Schuller (Johns Manville Corp.), Denver, Colorado and marketed as Microquartz™ fibers or as Q-fiber™. These fibers have an average diameter of 1.7 microns. However, silica fibers having diameters ranging from 1 to 6 microns are useful in the present invention. While boron nitride is considered to be the preferred boron source, it is believed that $SiB_x$, $B_4C$, $B_2O_3$, and B and other boron sources can also be used. It is preferred that B be present in an amount from about 0.4% to about 2% by weight. Boron nitride is believed to be preferred because it is believed, due to its stability, that it permits a more uniform fusion to fiber junction and yields superior bonding and uniform porosity. In addition, aluminaborosilicate fibers may be used and are available from 3M Company marketed under the tradename AB-312™ which contains 62% (±2.0%) $Al_2O_3$, 14% (±2.0%) $B_2O_3$ and 24% (±2.0%) $SiO_2$.

These fibers are available and useful in the present invention i diameters ranging from 3 to 12 microns.

The preferred composition comprised of: 21% by weight alumina fiber; 74% by weight silica fiber; 2% by weight (600 grit) silicon carbide; and 2.85% by weight boron nitride is also available commercially in densities of 3 to 64 lbs./ft.$^3$ (plus/minus ¾ lb.) from Lockheed Missiles and Space Company, Inc., Sunnyvale, California ("Lockheed") under the trade name "HTP" (High Temperature Performance). For example, Lockheed commercially sells "HTP-12-22" (12 lb./ft.$^3$ density silica/alumina fiber ratio of 78/22), "HTP-12-35" (12 lb./ft.$^3$ density in a silica/alumina fiber ratio of 65/35) and "HTP-12-45" (12 lb./ft.$^3$ density in silica/alumina fiber ratio of 55/45).

Venus Dental Materials manufactures the above types of Ultra-low density fused-fibrous ceramics under the trade name P.R.I.M.M™ (Polymeric Rigid Inorganic Matrix Material). Venus Dental Materials manufacturers P.R.I.M.M™ in densities varying from 4 lb./ft.$^3$ to 64 lb./ft.$^3$. P.R.I.M.M™ material is ground by mortar and pestle, or other grinding mechanism, then sieved into different particulate sizes. An optimum sieved particulate size for P.R.I.M.M™ material (16 lb./ft.$^3$ density) is approximately 180 μm in diameter. However, optimum particle sizes are believed to be dependent upon the surface tension and viscosity of the binder used in a particular application and P.R.I.M.M™ material density.

The compressive strength (MN/m$^2$) and tensile strength (MN/m$^2$) of an embodiment of the restorative material of the present invention (78% alumina, 22% silica, % 3 silicon carbide, 2.85% boron nitride at 16 lb./ft.$^3$ density) is compared in FIGS. 1a–4b to commercially available dental restorative materials: "LACITONE 199 DENTURE ACRYLIC" available from Dentsply International, Inc.; "RESTOLUX SP-4 COMPOSITE RESIN" (Chopped Fibers) available from Lee Pharmaceuticals; "HERCULITE XRV" (Kerr) composite resin available from Kerr Manufacturing Co.; "TYTIN AMALGAM ALLOY" available from Kerr Manufacturing Co.

The tensile and compressive strength values of the commercially available materials used for comparison were taken from product information sheets provided by the manufacturers. The method used to determine the tensile strength of the material of the present invention was the Brazilian Test as described in the literature of *Craig*. (See, Craig; R. G. (1989): *Restorative Dental Materials*, 8 Ed., St. Louis: Mosby, 65-12; 255-92 which is hereby incorporated by reference.)

FIGS. 1a–4b illustrate the compressive and tensile strength advantage of the material of the present invention over several commercially available materials. As shown and tested, the material of the present invention has a compressive strength equal to or greater than about 550 MN/m$^2$ and a tensile strength equal to or greater than about 150 MN/m$^2$.

In relation to mixing the filler component of the present invention with a

1*Raw Material binder to form the composite of the present invention, approximately 1.0 gram of P.R.I.M.M.™ fused-fibrous ceramic product, having a density of 16 lb./ft.$^3$, was added to approximately 1 gram of GTE resin available from Dentsply and mixed until a complete wetting occurred. It should be noted, that this resin ratio was found to be ideal for easy incorporation and loading beyond this point was detrimental to the ultimate handling of the material. In fact, at a point past this ratio, the composite became very thick and dry and the overloading resulted in unusable material. It is also believed that an increased particle cluster size improves the capillary action of the fibers aligned for an easier incorporation of the resin into the fibers.

It has also been found to be preferable, that once the fibers have been thoroughly mixed into the resin, a known amount of colloidal silica (0.3 grams) ("CABOT-CABOSIL LM 130" fumed silica) was incorporated until the material had a consistency similar to that of currently marketed composite resins. However, unlike currently available composite resins, this mixture proved to be packable and handled much the same way as an amalgam alloy.

It is also believed that the addition of a silanation agent improves the fiber to resin bond. For example, an organofunctional silanation agent (Union Carbide-Silane A-174) was added to the composite. Specifically, 0.1 gram of the silane was added to 1.0 gram of resin prior to mixing it with the fibers. The result of this action produced an intact fiber resin interface bond following the fracturing of the sample.

Figure 5:
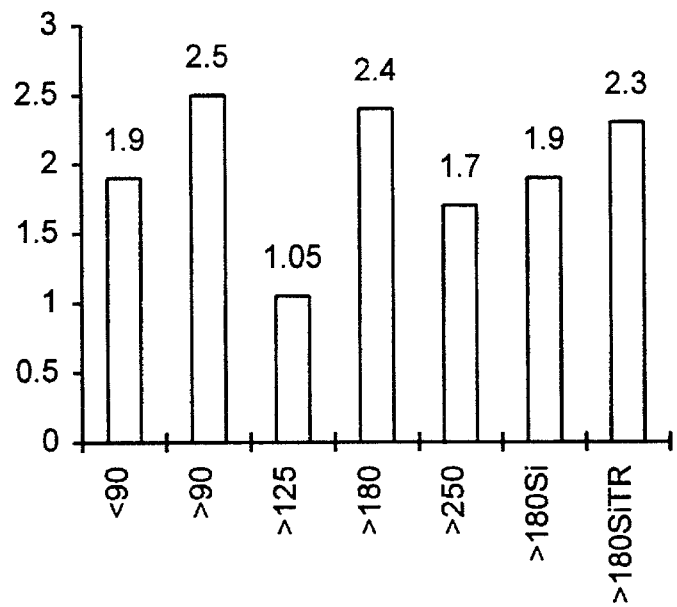
FIG. 5 is a table of the Ideal Modulous form at density 16—Particle size>180 um—with silica (Colloidal) and Silinated Resin.
Figure 6:
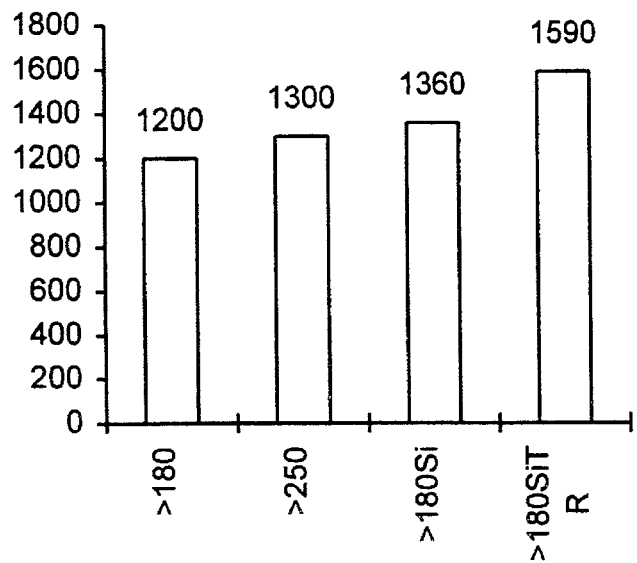
FIG. 6 is a table showing that the compressive strength exhibited significant improvement with the addition of Colloidal Silica and presilination of the resin.
Figure 7:
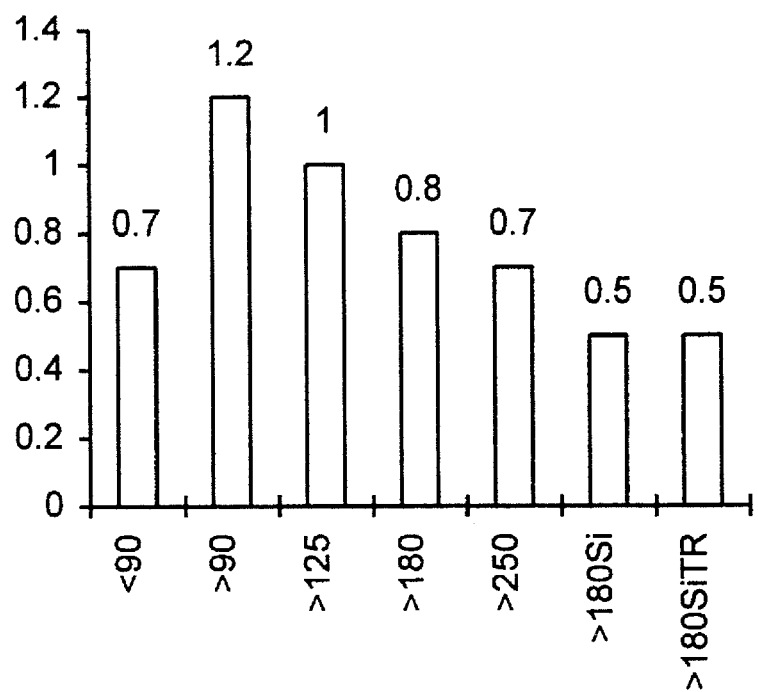
FIG. 7 is a table showing that the surface roughness decreased significantly with the addition of silica (Colloidal).

It has also been found that the mean particle size (microns) effects the flexural modulus (Pa×10$^{10}$), compressive strength (MN/m$^2$), and surface roughness (Ra). Shown in FIGS. 5–7, is the filler component of the present invention at 16 lb./ft.$^3$ density (1:1 filler/resin mixture) for different particle sizes (microns). Note, as used below, "Si" means the material includes colloidal silica and "SiTR" means it includes colloidal silica and that the resin was silanated.

A comparison of the properties of the filler component of the present invention as compared to prior art filler components is shown in FIG. 8.

FIG. 8

| Product | P.R.I.M.M.™ | Restolux HP-4 | Z100 (3M) | XRV Herco. | TPH Prisma | Heliomolar | Charisma |
|---|---|---|---|---|---|---|---|
| Filler | Alumina/Silica (Fused Glass Fibers) | Glass Ceramic Fibers | Zirconia/Silica | Barium Glass | Barium Glass | SiO$_3$ | Barium Glass/ Microglass |
| Filler Loading Wt (%) | 60 | 68.5 | 66 | 56 | 53 | 38 | 73 |
| Average Particle Size (microns) | 180/0.04 | 300 | 0.6 | 0.6 | 1 | Microfil | 0.7 |
| Diametral Tensile (MPa) | 82 | | 83 | 81 | 72 | 47 | 77 |
| Compressive Strength (MPa) | 560 | | 448 | 324 | 375 | 436 | 399 |
| Hardness (Kg/mm$^2$) | 50 | 125 | 78.3 | 53.3 | 43.5 | 35.9 | |
| Y-Modulous (Pa) | 2.5 × 10$^{10}$ | 23 × 10$^9$ | 13 × 10$^9$ | 7.6 × 10$^9$ | 5.7 × 10$^9$ | 4.3 × 10$^9$ | |
| Surface | 0.30 | 1.19 | 0.27 | 0.12 | 0.29 | 0.13 | |

-continued

FIG. 8

| Product | P.R.I.M.M.™ | Restolux HP-4 | Z100 (3M) | XRV Herco. | TPH Prisma | Heliomolar | Charisma |
|---|---|---|---|---|---|---|---|
| Roughness (Ra) | | | | | | | |
| Coeff of Thermal Expansion × $10^6$ unit/unit/°C. | 10 | 17 | 17 | 27 | 30 | 52 | 38 |
| Radiopacity | Yes | Yes | Yes | Yes | Yes | Yes | Yes |

What I claimed is:

1. In a method for the direct filling of a cavity in a tooth, wherein said method includes filling said cavity with an initially liquid, settable filing material comprising a filler and a binder admixed therewith, thereafter permitting said material to harden in situ, the improvement in said method comprising utilizing as the predominant component of said filler, a fused-fibrous matrix compound comprised of:

from about 1% to about 50% by weight alumina;

from about 50% to about 98% by weight silica; and from about 1% to about 5% by weight boron nitride.

2. The method of claim 1 wherein said fused-fibrous matrix compound is further comprised of silicon carbide.

3. The method of claim 1 wherein the fused-fibrous matrix compound is comprised from about 15% to about 30% by weight alumina and from about 65% to about 85% silica.

4. The method of claim 1 wherein the fused-fibrous matrix compound is comprised of alumina and silica in a ratio of 22:78.

5. A dental restorative composition comprising:

a binder; and a fused-fibrous matrix compound filler, said filler comprised of about 1% to about 50% by weight alumina, from about 50% to about 98% by weight silica, and boron.

6. The composition of claim 5 wherein said fused-fibrous matrix compound filler further comprises silicon carbide.

7. The composition of claim 5 wherein the filler is comprised of about 15% to about 30% by weight alumina and about 65% to about 85% silica.

8. The composition of claim 5 wherein the filler is comprised of about 21% by weight alumina and about 74% by weight silica.

9. A method for the filling of a cavity in a tooth comprising:

(a) filling said cavity with a settable filling material comprising a binder and filler, wherein said filler is a fused-fibrous matrix compound comprising from about 15% to about 30% by weight alumina; from about 65% to about 85% by weight silica; from about 1% to about 3% by weight silicon carbide, and from about 1% to about 5% by weight boron nitride; and (b) thereafter allowing said material to harden.

10. The method of claim 9 wherein the filler is comprised of from about 21% by weight alumina and about 74% by weight silica.

11. The method of claim 9 wherein the filler is comprised of alumina and silica in a ratio of 22:78.

12. A fused-fibrous matrix compound ceramic dental restorative composition comprising:

alumina, silica and boron.

13. The composition of claim 12 further comprising silicon carbide.

14. The composition of claim 12 comprised of about 2.85% by weight boron nitride.

15. The composition of claim 12 comprised of about 21% by weight alumina.

16. The composition of claim 12 comprised of about 74% by weight silica.

17. A fused-fibrous matrix compound dental restorative composition manufactured from:

alumina fibers;

silica fibers; and a fusion source, whereby said composition has a compressive strength equal to or greater than about 500 $MN/m^2$.

18. The composition of claim 17 comprising from about 1% to about 50% by weight alumina fibers.

19. The composition of claim 17 comprising from about 50% to about 98% by weight silica fibers.

20. The composition of claim 17 wherein the alumina fibers range from about 1 to about 20 microns in average diameter.

21. The composition of claim 17 wherein the silica fibers rage from about 1 to about 6 microns in average diameter.

* * * * *

UNITED STATES PATENT AND TRADEMARK OFFICE
CERTIFICATE OF CORRECTION

PATENT NO: 5,621,035

DATED: April 15, 1997

INVENTOR(S): Mark B. Lyles; Ronald G. Ritsco

It is certified that error appears in the above-identified patent and that said Letters Patent are hereby corrected as shown below:

Assignee: Materials Evolution and Development USA, Inc.

Signed and Sealed this

Seventeenth Day of April, 2001

*Attest:*

NICHOLAS P. GODICI

*Attesting Officer*     *Acting Director of the United States Patent and Trademark Office*